United States Patent
Davies et al.

(10) Patent No.: US 7,891,578 B2
(45) Date of Patent: Feb. 22, 2011

(54) LIQUID FORMATIONS FOR ELECTROHYDRODYMANIC SPRAYING CONTAINING POLYMER AND SUSPENDED PARTICLES

(75) Inventors: David Neville Davies, Oxford (GB); Marie Pollard, Ontario (CA); Ronald Alan Coffee, Haslemere (GB)

(73) Assignee: Battelle Memorial Institute, Columbus, OH (US)

( * ) Notice: Subject to any disclaimer, the term of this patent is extended or adjusted under 35 U.S.C. 154(b) by 591 days.

(21) Appl. No.: 10/472,721

(22) PCT Filed: Mar. 22, 2002

(86) PCT No.: PCT/GB02/01384

§ 371 (c)(1),
(2), (4) Date: Feb. 6, 2004

(87) PCT Pub. No.: WO02/076424

PCT Pub. Date: Oct. 3, 2002

(65) Prior Publication Data

US 2004/0135015 A1     Jul. 15, 2004

(30) Foreign Application Priority Data

Mar. 22, 2001 (GB) ............................... 0107226.3
Oct. 2, 2001 (GB) ............................... 0123646.2

(51) Int. Cl.
*B05B 5/025* (2006.01)
(52) U.S. Cl. .................... 239/3; 239/332; 239/690; 239/708; 128/200.14

(58) Field of Classification Search ............... 239/3, 239/332, 690, 708; 128/200.14; 424/43, 424/486

See application file for complete search history.

(56) References Cited

U.S. PATENT DOCUMENTS

| 4,043,331 | A | 8/1977 | Martin et al. |
| 4,044,404 | A | 8/1977 | Martin et al. |
| 4,952,212 | A | 8/1990 | Booth et al. |
| 5,873,523 | A | 2/1999 | Gomez et al. |
| 6,079,634 | A * | 6/2000 | Noakes et al. ............... 239/3 |
| 6,105,877 | A * | 8/2000 | Coffee ............................ 239/3 |
| 6,339,107 | B1 | 1/2002 | Belloni |
| 6,394,086 | B1 * | 5/2002 | Barnes et al. .......... 128/200.14 |
| 6,503,481 | B1 * | 1/2003 | Thurston et al. ........ 128/200.14 |
| 6,595,208 | B1 * | 7/2003 | Coffee et al. ................ 239/690 |
| 6,684,879 | B1 * | 2/2004 | Coffee et al. .......... 128/200.14 |
| 6,709,650 | B1 * | 3/2004 | Sutton et al. .................. 424/46 |
| 2003/0173219 | A1 | 9/2003 | Davies et al. |

FOREIGN PATENT DOCUMENTS

| EP | 0 444 778 A1 | 9/1991 |
| EP | 0 919 242 A2 | 6/1999 |
| GB | 1 569 707 | 6/1980 |
| GB | 2 273 893 A | 7/1994 |
| WO | WO 89 07603 | 8/1989 |

(Continued)

*Primary Examiner*—Steven J Ganey
(74) *Attorney, Agent, or Firm*—Frost Brown Todd LLC

(57) ABSTRACT

A method of providing a droplet spray, includes supplying a liquid polymer formulation within which substantially inert particulate material is suspended to an outlet and subjecting liquid issuing from the outlet to an electric field that causes the liquid to break up into droplets.

5 Claims, 17 Drawing Sheets

FOREIGN PATENT DOCUMENTS

| | | |
|---|---|---|
| WO | WO 94 12285 | 6/1994 |
| WO | WO 96 19197 | 6/1996 |
| WO | WO 96 30068 | 10/1996 |
| WO | WO 98 03267 | 1/1998 |
| WO | WO 99 49923 | 10/1999 |
| WO | WO 00 35524 | 6/2000 |
| WO | WO0035524 * | 6/2000 |
| WO | WO 00 66206 | 11/2000 |
| WO | WO 01 74431 A2 | 10/2001 |
| WO | WO 02 43750 A2 | 6/2002 |
| WO | WO 03 082242 A2 | 10/2003 |

* cited by examiner

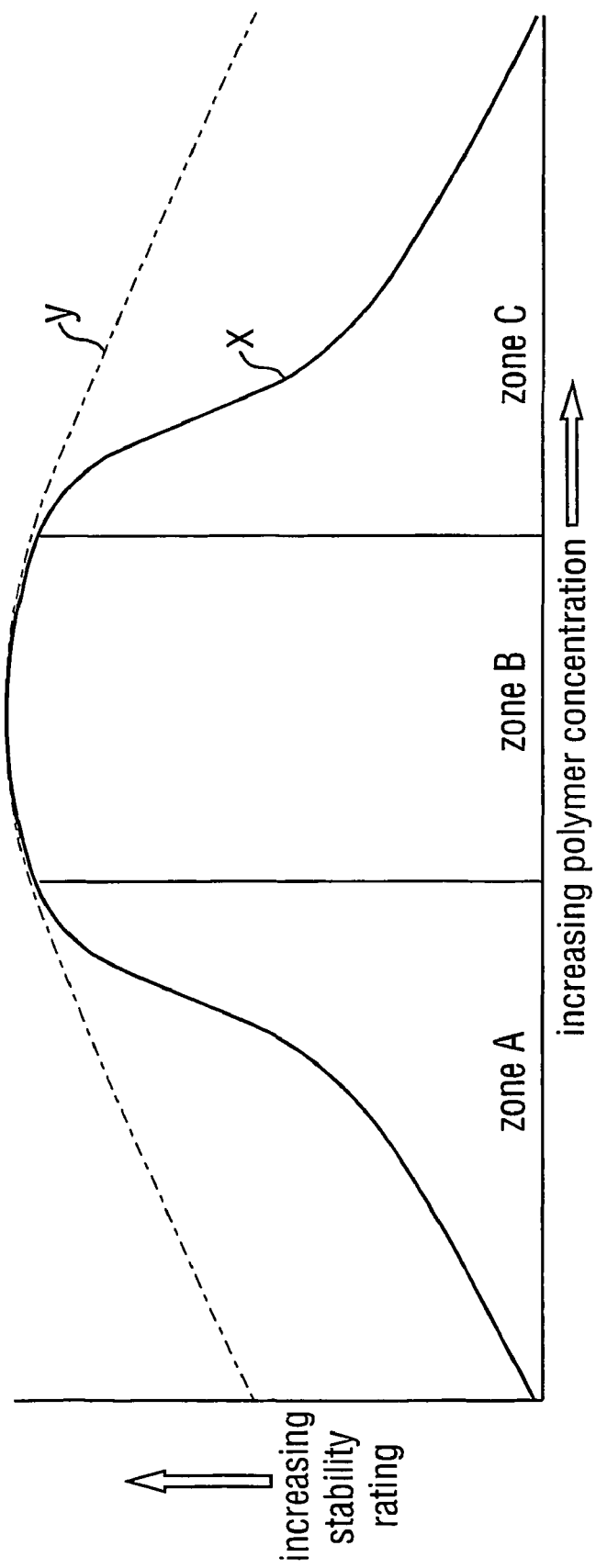

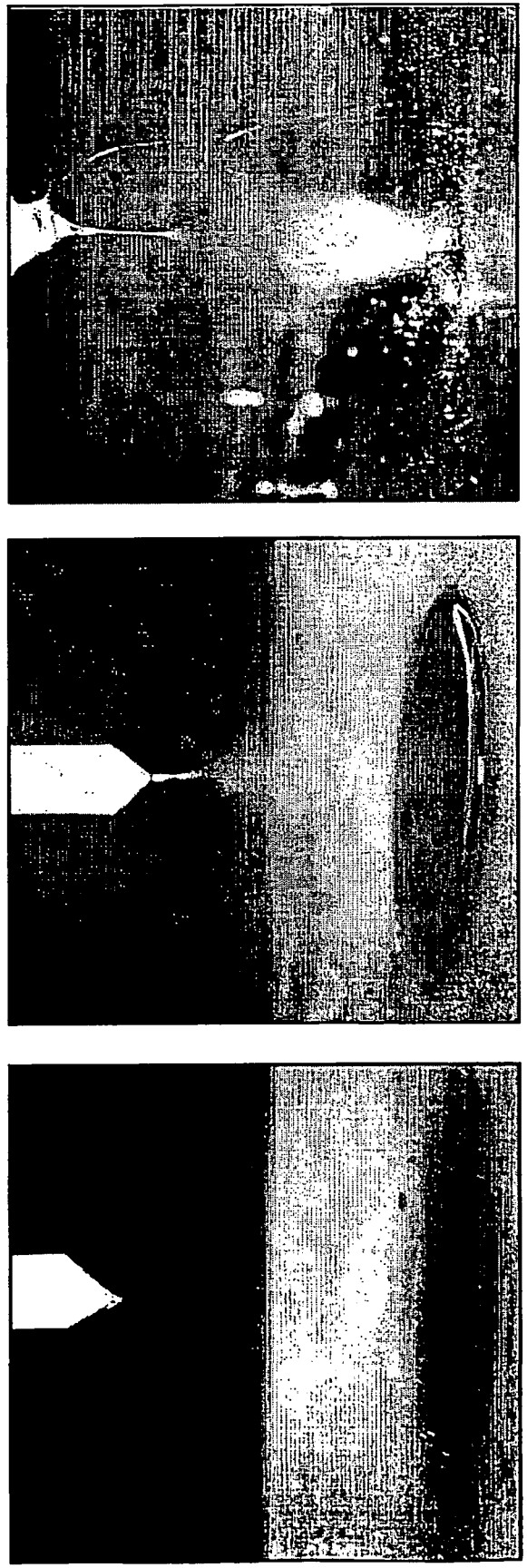

Droplet Spread @ 7.2ml/hr

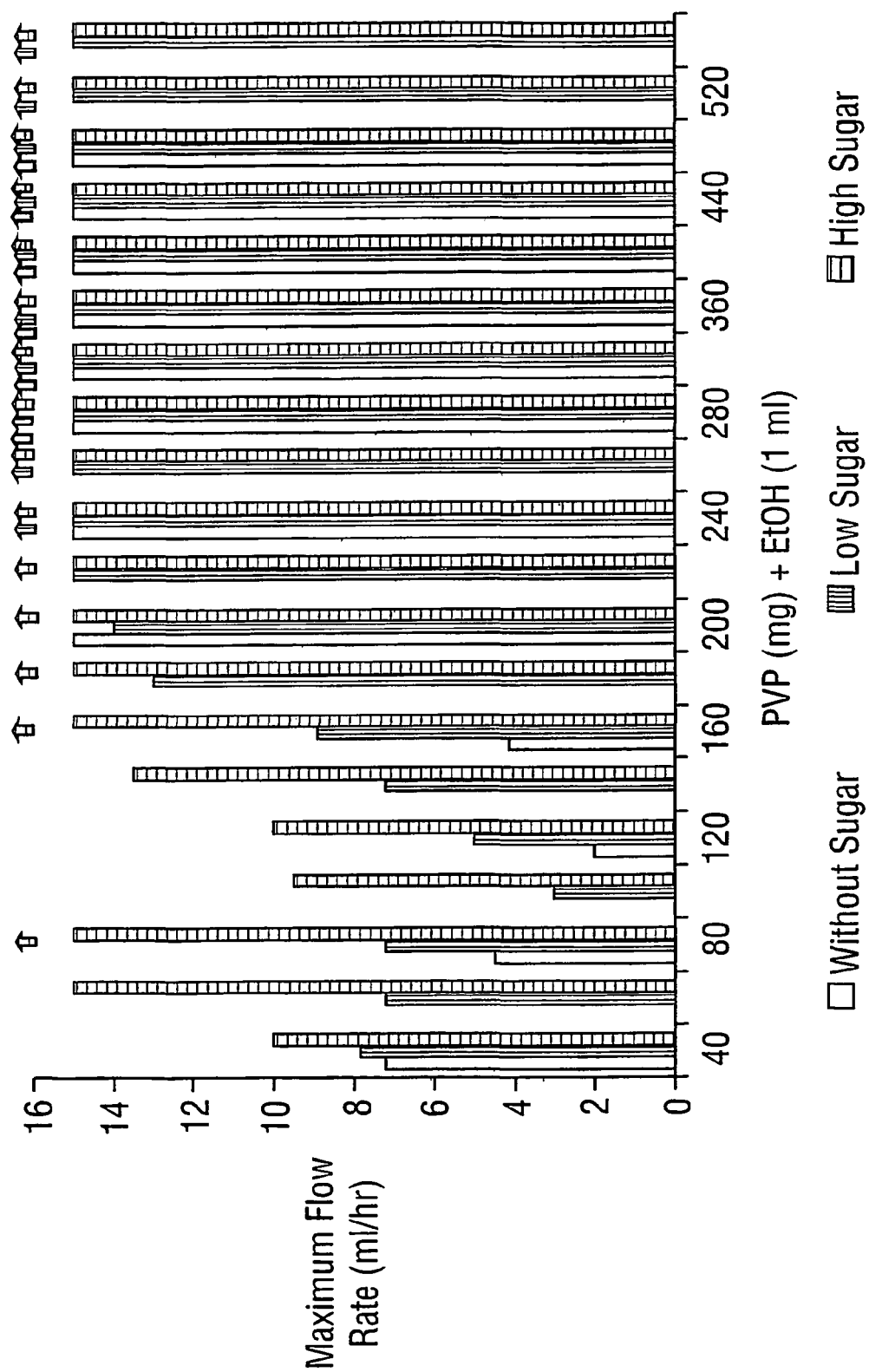

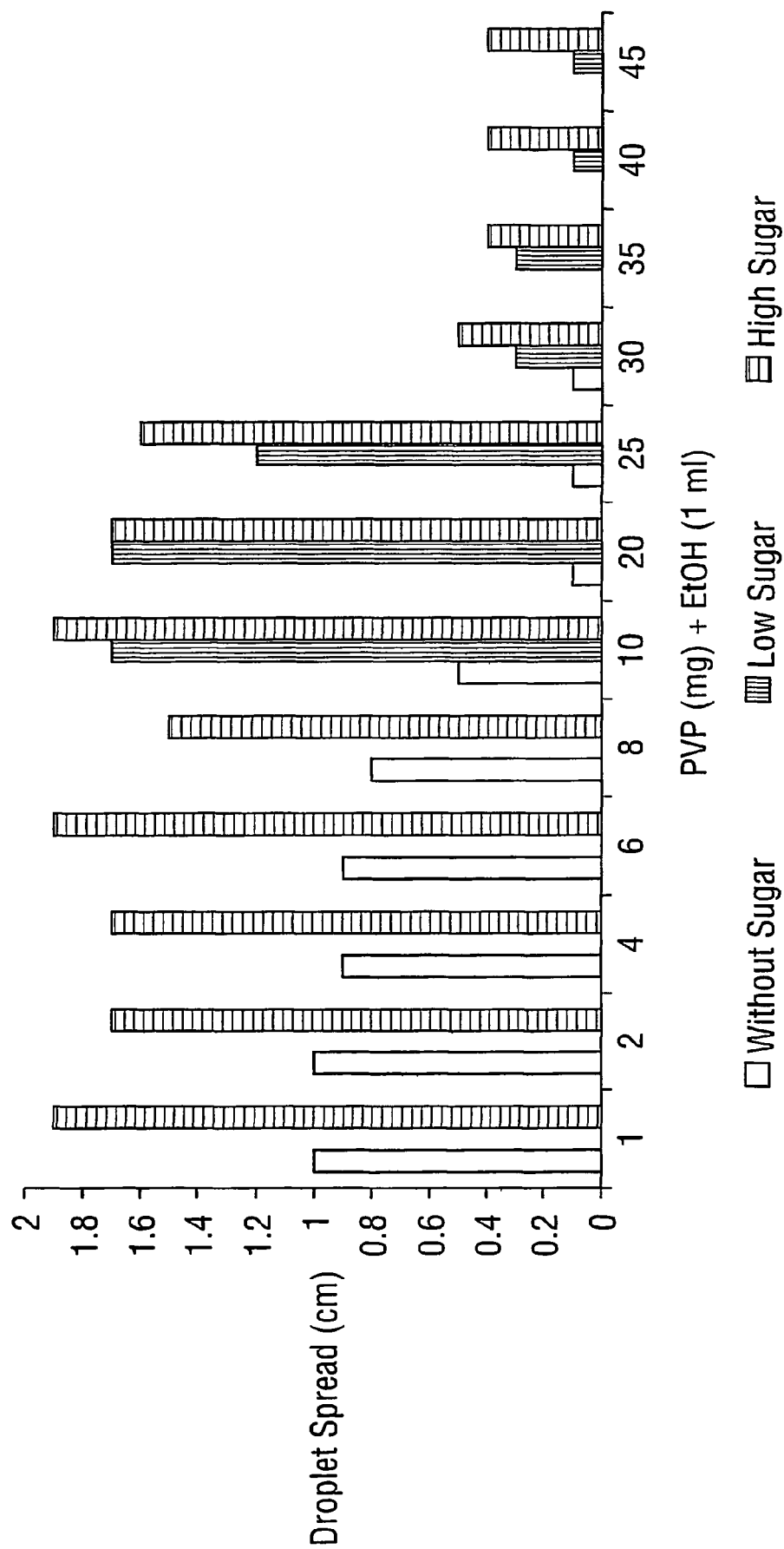

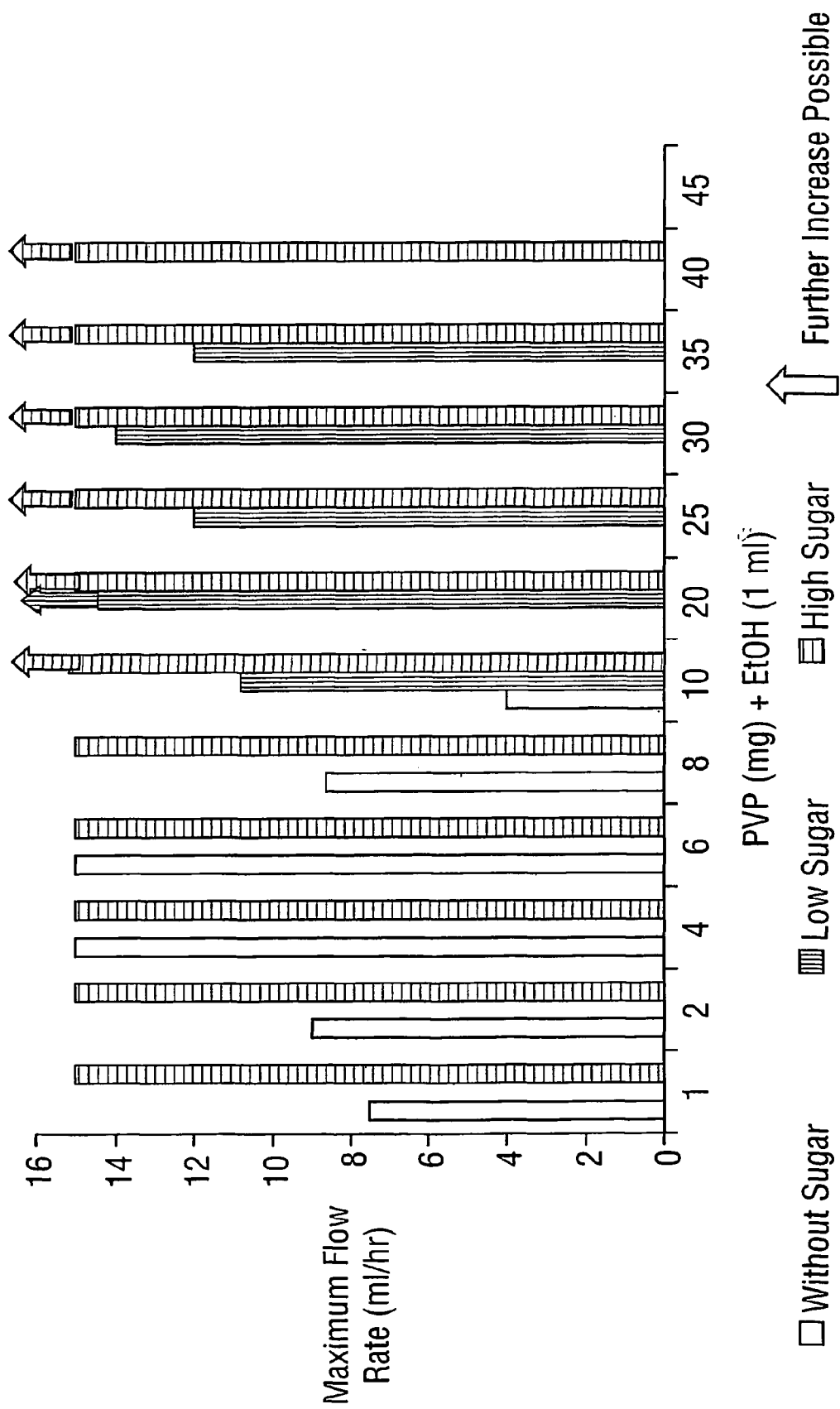

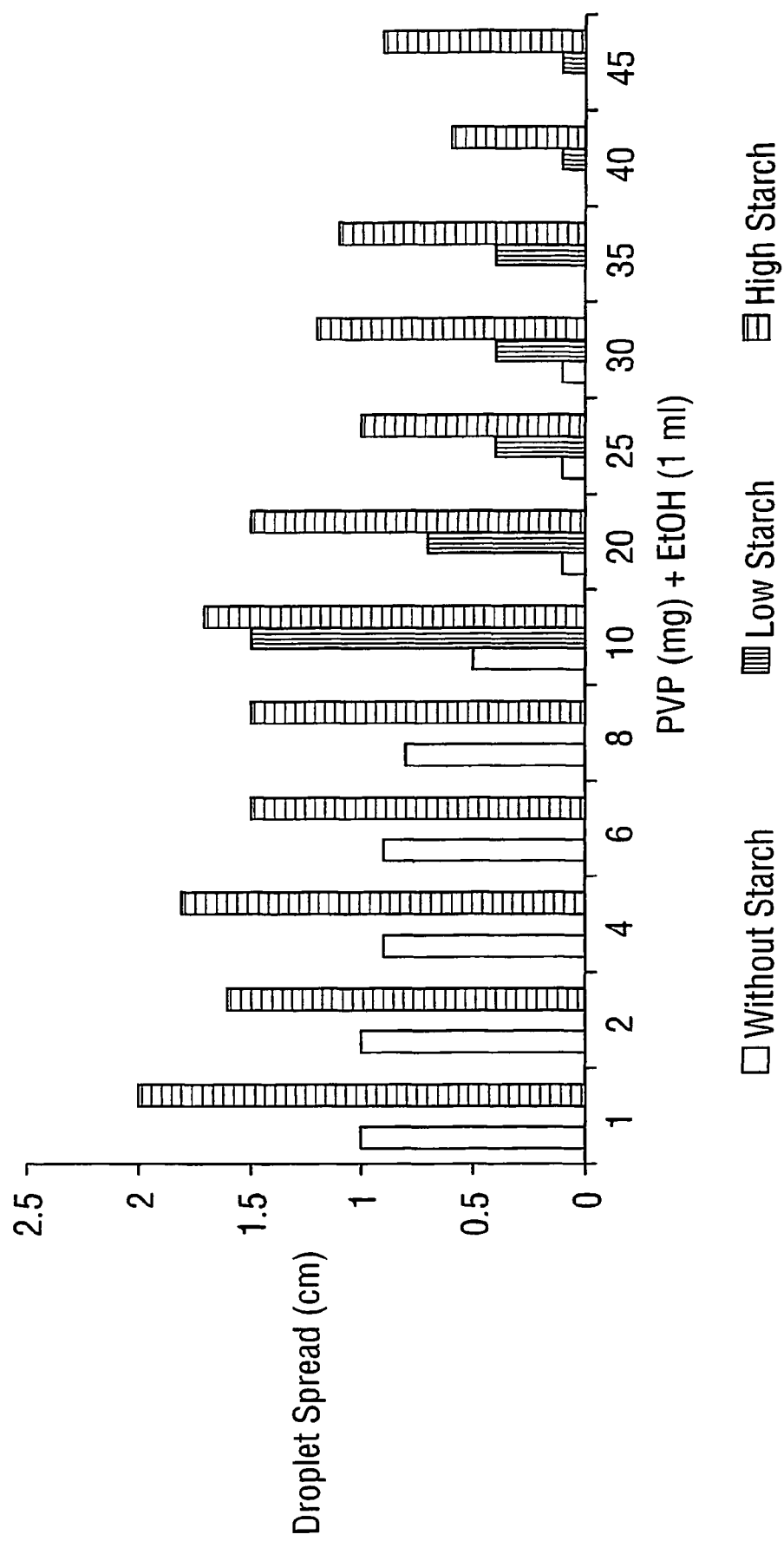

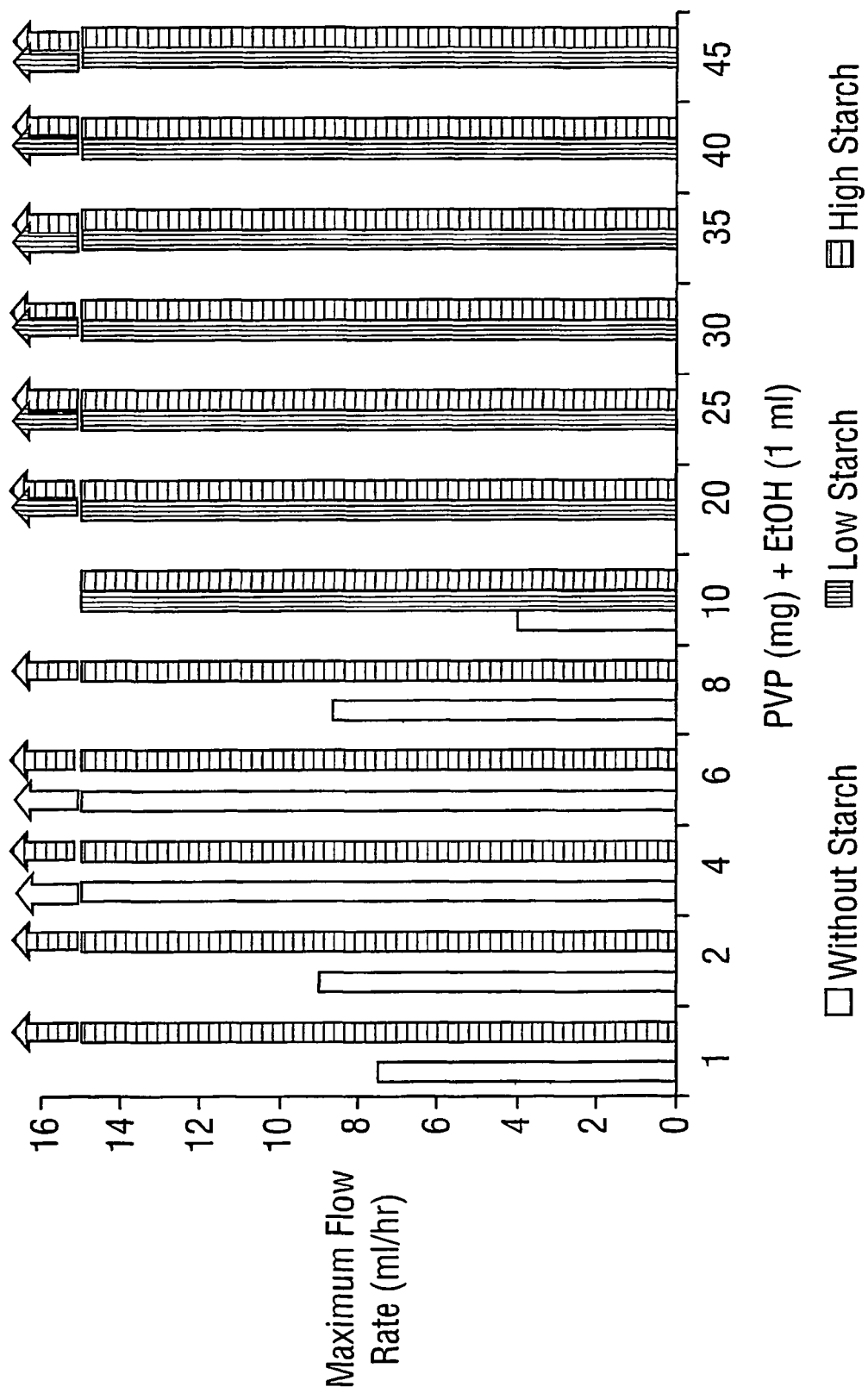

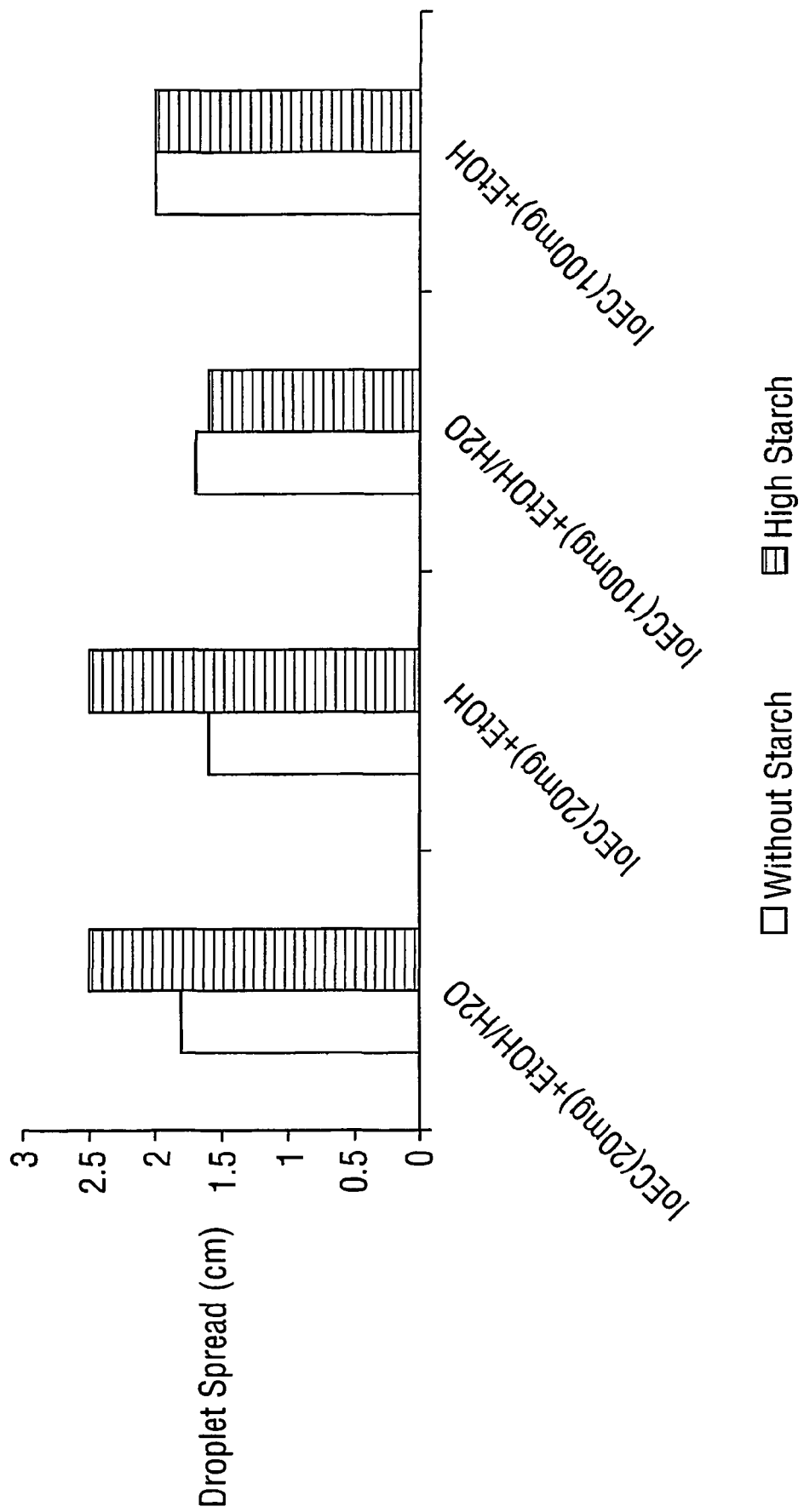

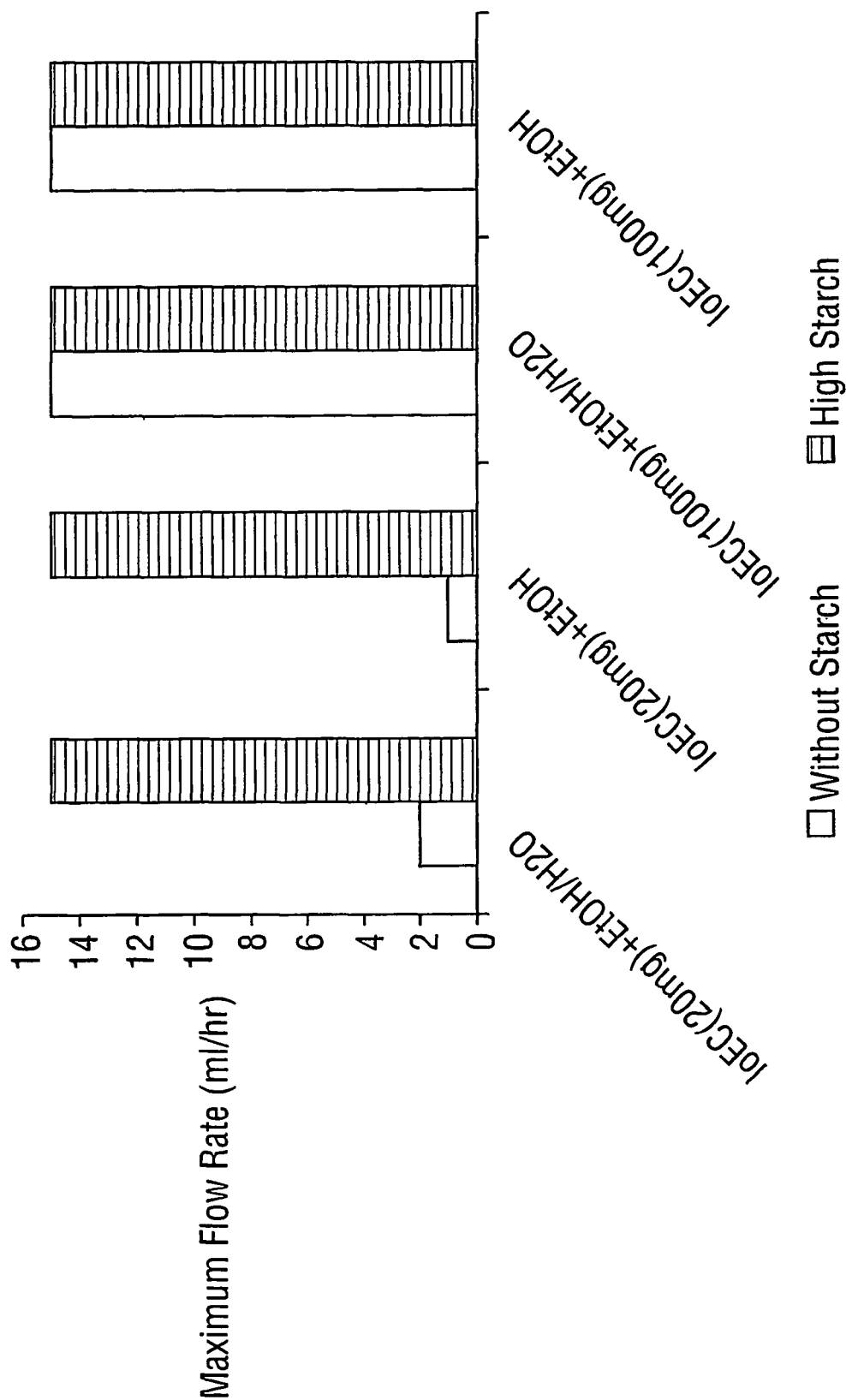

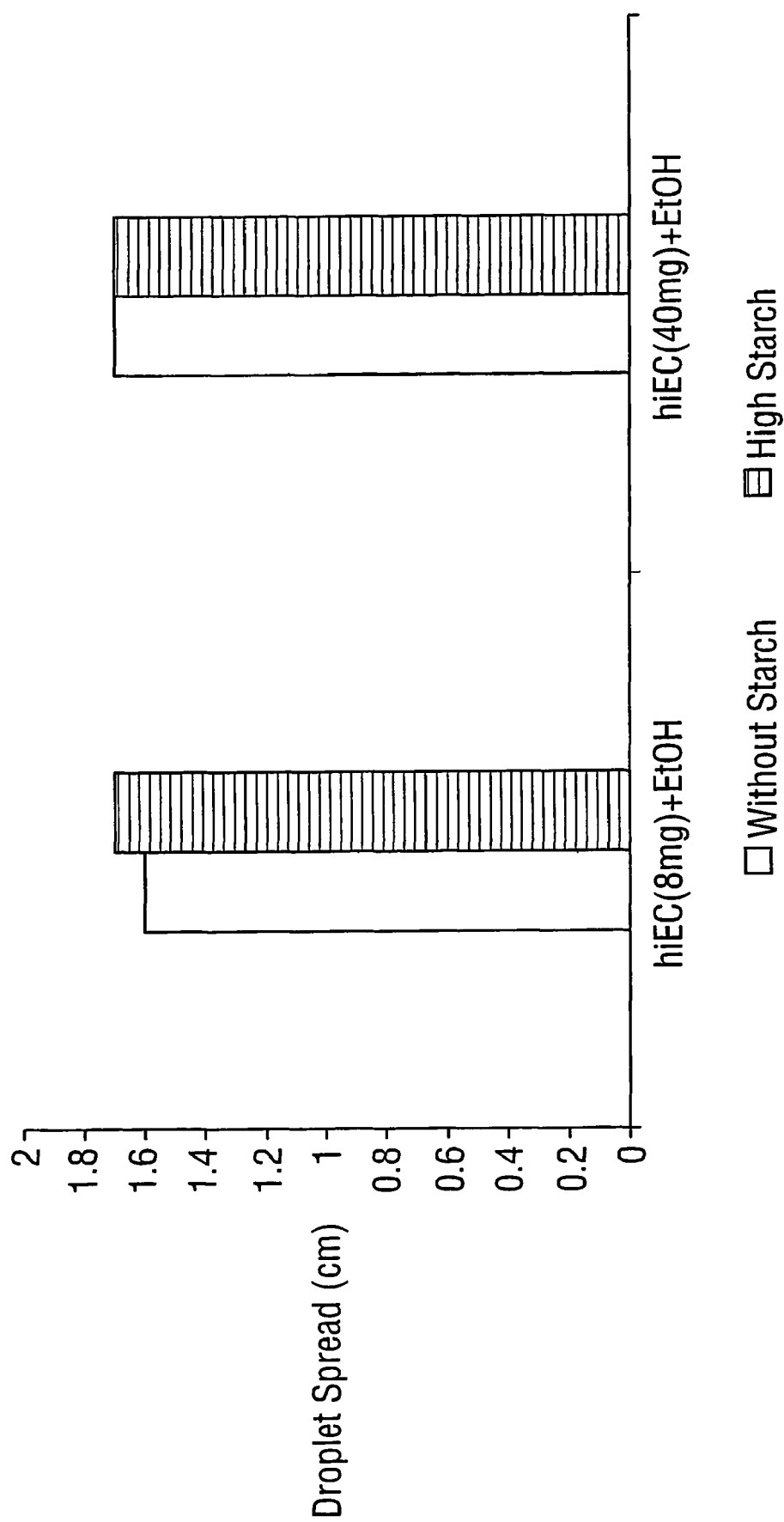

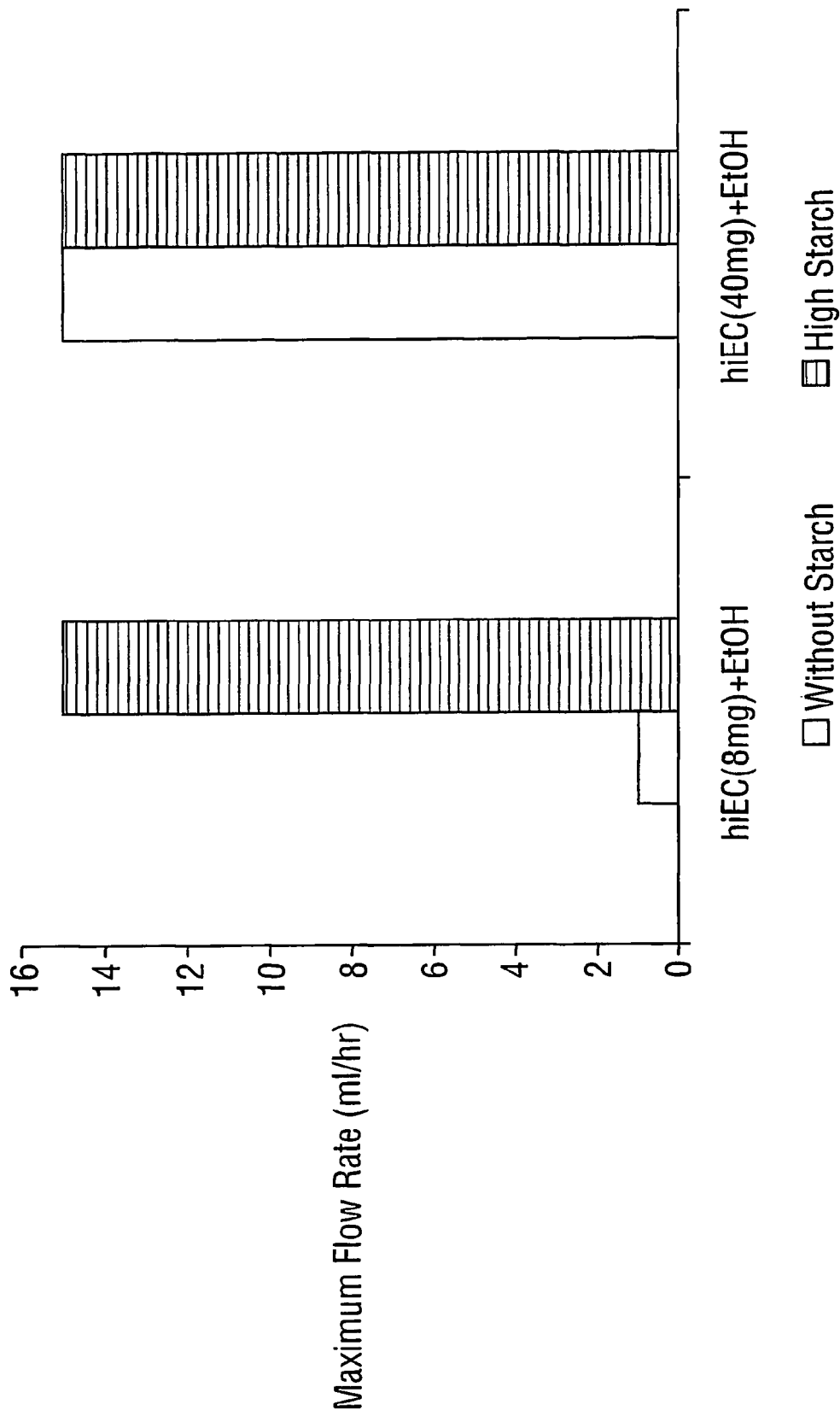

LIQUID FORMATIONS FOR ELECTROHYDRODYMANIC SPRAYING CONTAINING POLYMER AND SUSPENDED PARTICLES

This invention relates to formulations for use in electrohydrodynamic processing.

Electrohydrodynamic (EHD) processing is described in detail in, for example, GB-A-1569707. In this process, a dispersed spray or cloud of droplets which are all of substantially the same size (monodispersed) is produced by subjecting liquid emerging from an outlet or nozzle to an electric field.

Many applications for electrohydrodynamic processing have been proposed. One example which takes advantage of the monodispersed nature of the mist or cloud of droplets is the field of inhalers. In this field, electrohydrodynamic processing enables control over the size of droplets (by for example, controlling the liquid flow rate and/or applied voltage) which, in combination with the monodispersed nature of the mist or cloud, enables targeting more accurately of the droplets to a specific part of the respiratory system. An example of a nasal inhaler is described in WO 00/35524. Another application of electrohydrodynamic processing is in the topical application of medicaments or wound dressings as described in, for example, WO 98/03267.

In one aspect, the present invention provides a method of controlling the characteristics of a cloud or spray of droplets produced by electrohydrodynamic processing by controlling the formulation of the liquid used in the electrohydrodynamic processing.

In one aspect the present invention provides a formulation for use in electrohydrodynamic processing, wherein the formulation comprises a liquid comprising a polymer and particulate material in suspension within the liquid.

In another aspect, the present invention provides a formulation for use in electrohydrodynamic processing, wherein the liquid comprises a polymer and, in addition to any active ingredient, particulate material suspended within the liquid.

The liquid may be, for example, a polymer melt or polymer solution.

In one aspect, the present invention provides a formulation for use in electrohydrodynamic (EHD) processing, wherein the formulation comprises a liquid comprising a solvent such as ethanol, a polymer and particulate material comprising at least particles of a substantially inert material such as, for example, sugar, starch, polymer beads.

As used herein, the term "substantially inert material" refers to a material that does not form an active ingredient of the formulation, that is, although the substantially inert material may have an effect in use of a cloud or spray of droplets resulting from the EHD processing, that effect is not the intended effect of the formulation. Where the resulting cloud or spray of droplets is intended to be inhaled or applied topically to a human or animal body, then the substantially inert material should be biologically compatible material. As used herein, "biologically compatible" means that the material does not have an unintended significant adverse effect when droplets produced by EHD processing from a formulation containing that inert material are inhaled or applied topically in the intended manner.

In one aspect, the present invention provides a formulation for use in electrohydrodynamic processing when the formulation comprises a liquid solution comprising PVP in ethanol with particulate material in the form of sugar, starch or polymer beads suspended within the liquid.

Embodiments of the present invention will now be described, by way of example, with reference to the accompanying drawings, in which:

FIG. 2 shows a graph of stability against polymer concentration to illustrate the change in spraying characteristics when particulate material in suspension is incorporated into the formulation;

Figure 4C:
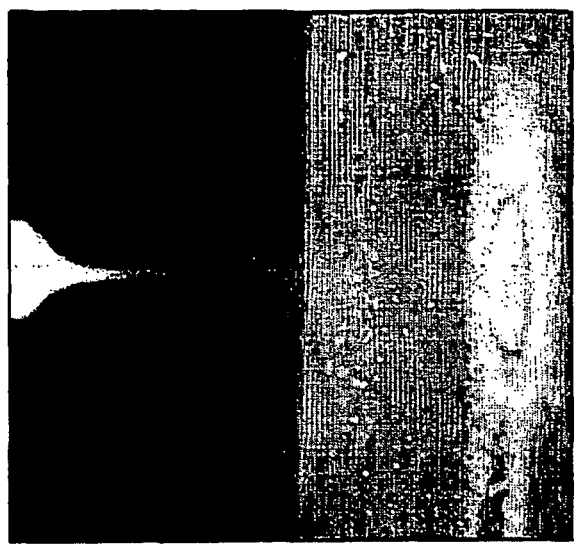
Figure 4B:
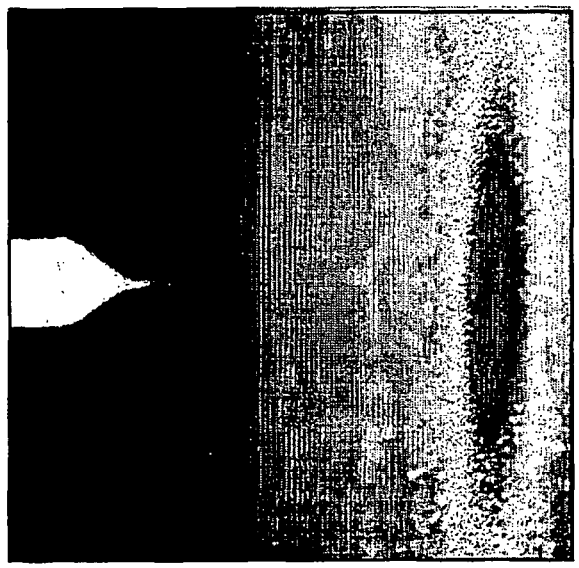
Figure 4A:
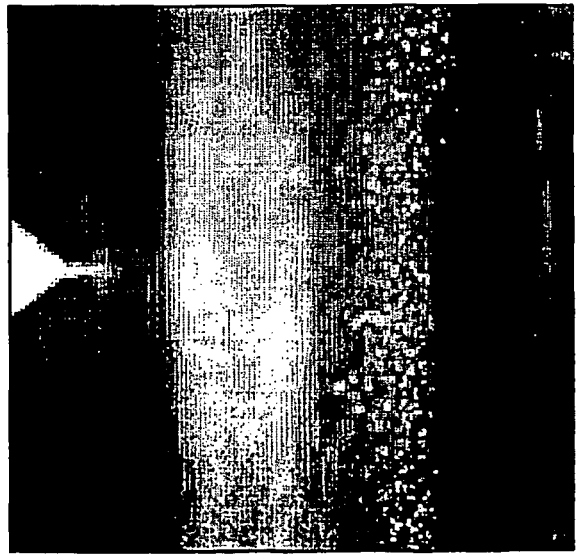
Figure 5A:
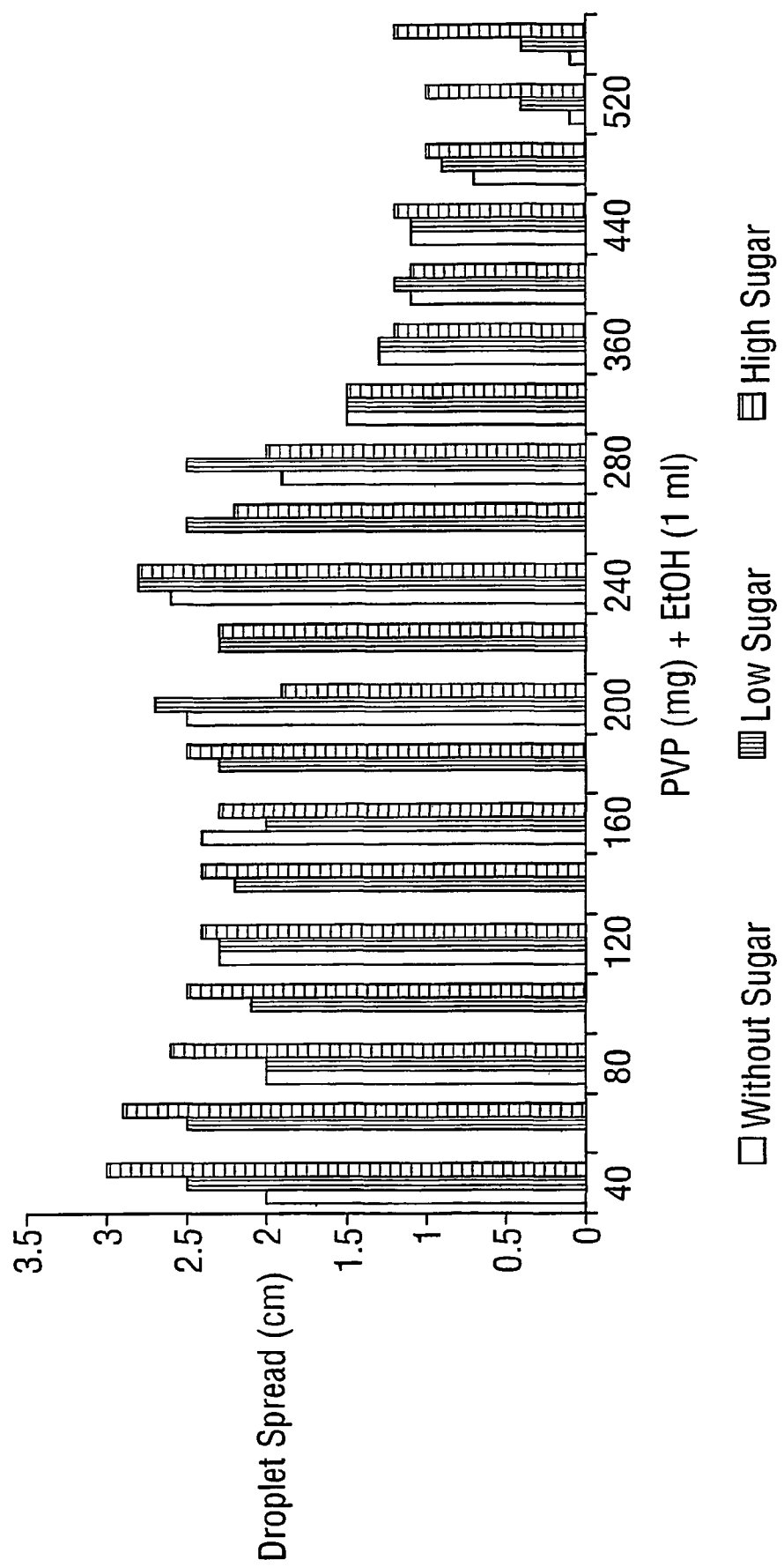
Figure 10B:
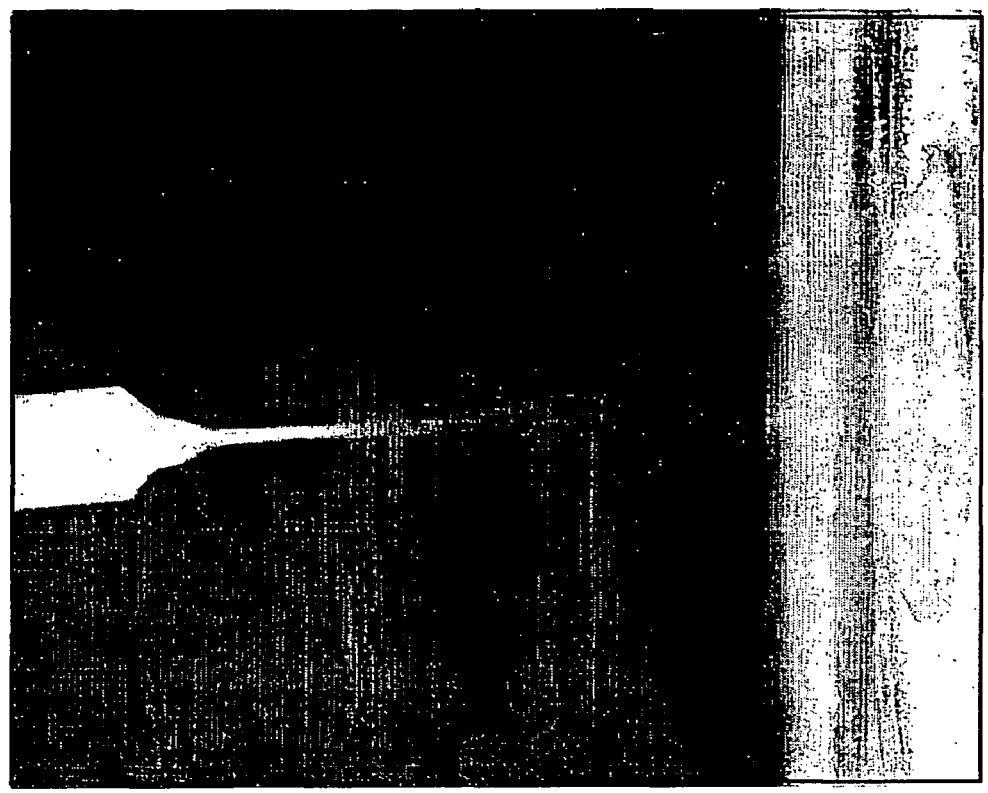
Figure 10A:
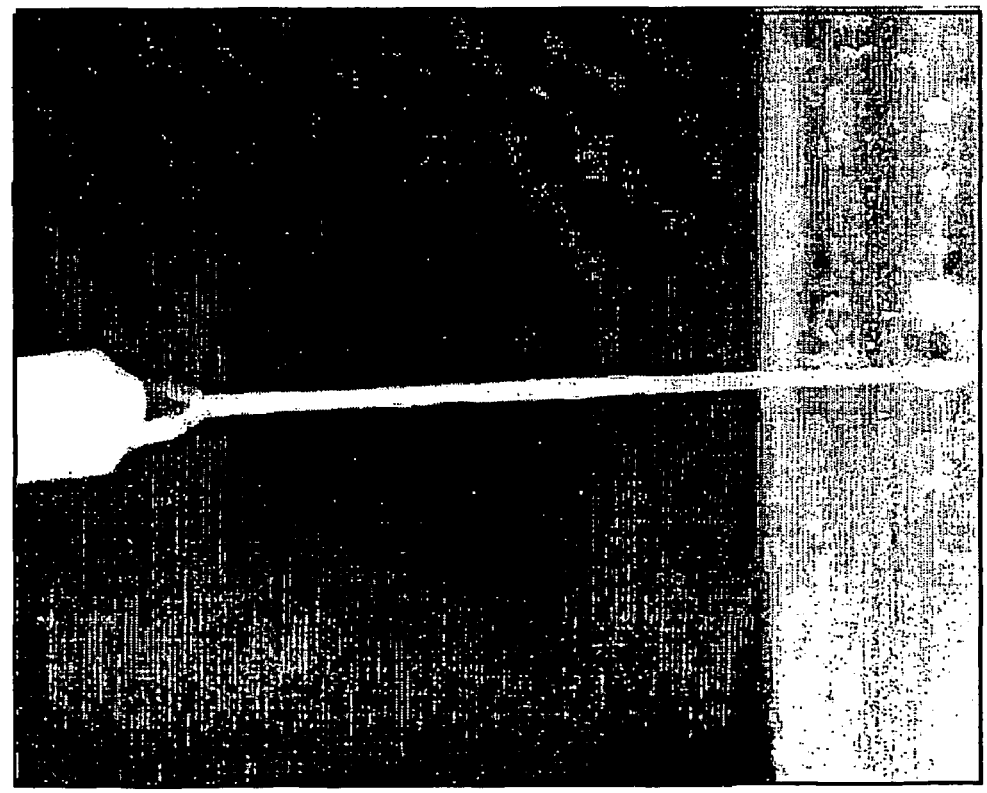
Figure 11B:
Figure 11A:
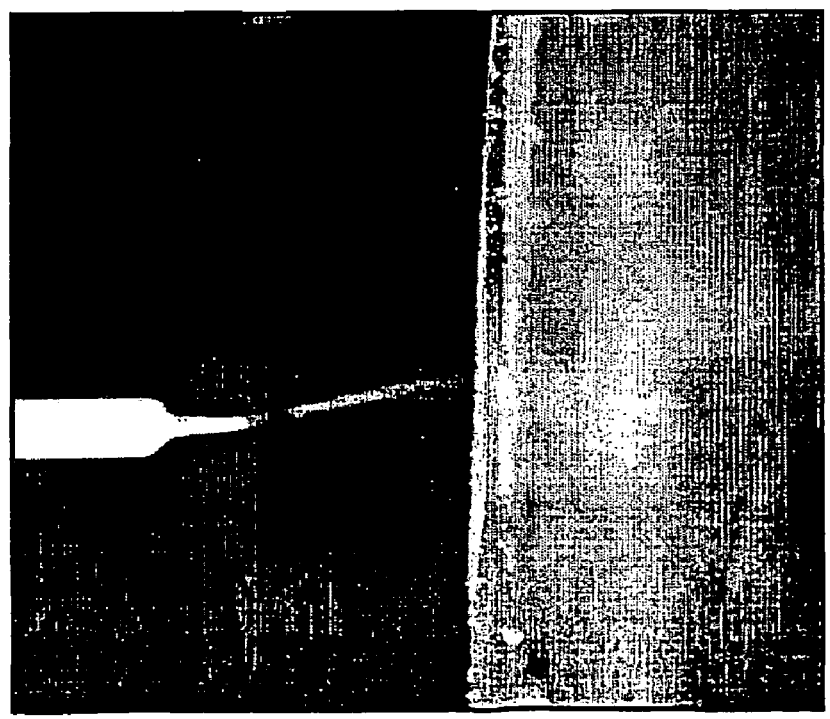
Figure 12:
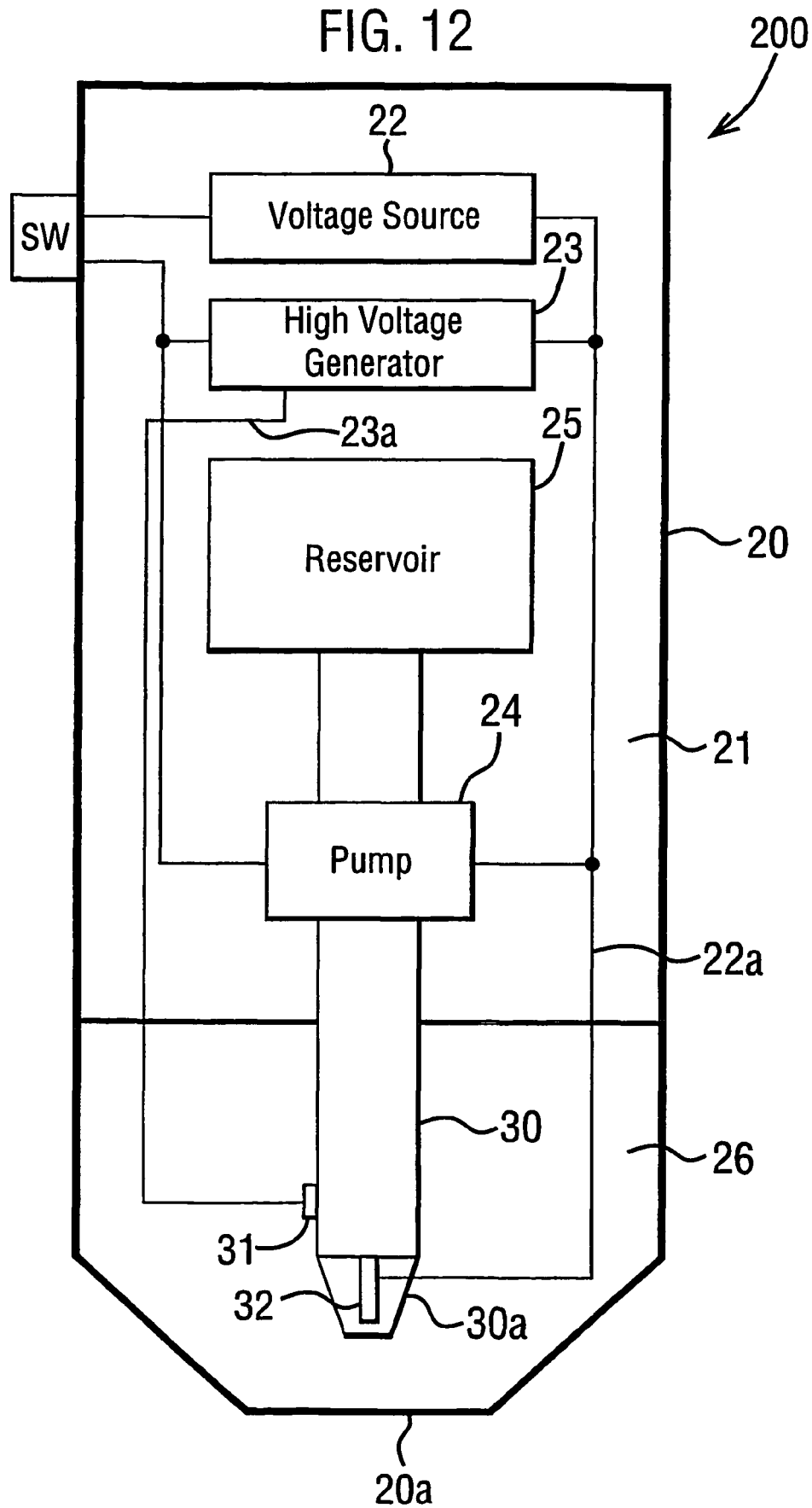

FIGS. 3a, b and c show photographs illustrating the spraying characteristics observed during EHD processing for zones a, b and c shown in FIG. 2 for a formulation that does not contain particulate material in suspension;

FIGS. 4a, b and c show photographs similar to FIGS. 3a, 3b and 3c, respectively, but for the case where the formulation incorporates particulate material in suspension;

FIGS. 5a and 5b show bar charts illustrating the effects on droplets spread and maximum flow rate, respectively, of suspending a first inert particulate material within a formulation for different concentrations of a first polymer within the formulation;

FIGS. 6a and 6b show bar charts similar to FIGS. 5a and 5b, respectively, for a formulation incorporating a second, different, polymer;

FIGS. 7a and 7b show bar charts similar to FIGS. 6a and 6b, respectively, for a formulation incorporating the same polymer but showing the effect of suspending a second different inert material within the formulation;

FIGS. 8a and 8b show bar charts similar to FIGS. 5a and 5b, respectively, where the formulation incorporates a third different polymer to show the effect of suspending the second inert particulate material within that polymer;

FIGS. 9a and 9b show bar charts similar to FIGS. 8a and 8b, respectively, where the formulation incorporates another polymer;

FIGS. 10a and 10b show photographs illustrating the spraying characteristics of a formulation comprising glycerol with FIG. 10a showing the spraying characteristics without incorporation of a particulate suspension and FIG. 10b showing the effect of incorporation of particulate suspension;

FIGS. 11a and 11b show photographs illustrating the spraying characteristics of a formulation comprising ethylcellulose with FIG. 11a showing the spraying characteristics without incorporation of a particulate suspension and FIG. 11b showing the effect of incorporation of a particulate suspension; and FIG. 12 shows a diagrammatic view (with a housing cutaway) of a dispensing device for dispensing a formulation by EHD processing.

Figure 1:
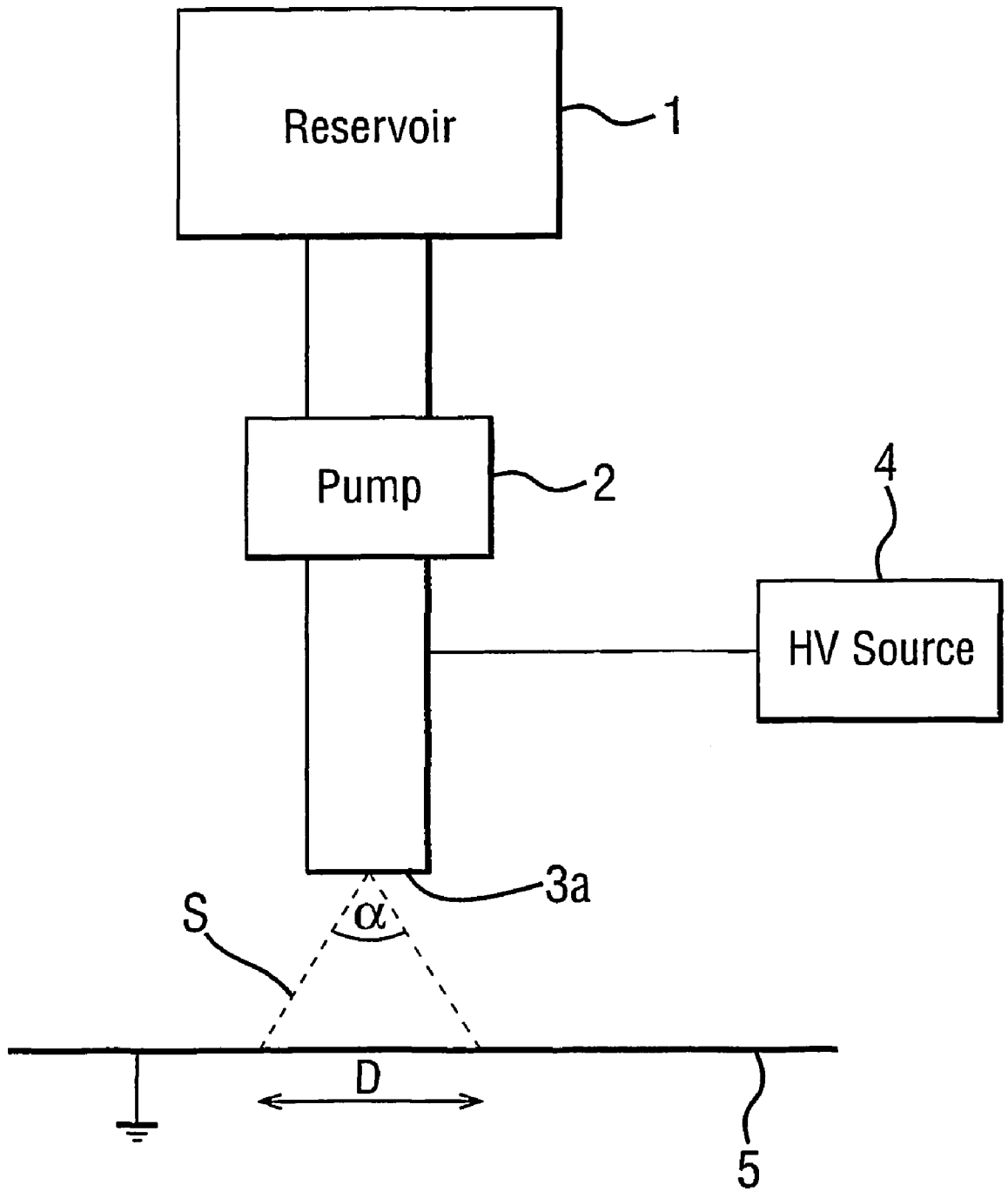
FIG. 1 shows a schematic diagram of apparatus for carrying out electrohydrodynamic processing.

Referring now to the drawings, FIG. 1 shows a very diagrammatic drawing of EHD processing apparatus used in the experiments to be described below. As shown in FIG. 1, the EHD processing apparatus comprises a reservoir 1 from which the formulation to be subject to electrohydrodynamic processing is pumped via a pump 2 to a metal capillary tube 3 having an outlet 3a. The metal capillary tube is coupled to a high voltage source 4 which, in this example, supplies a voltage in the range of 7 to 8 kilovolts. The outlet 3a is positioned above an earthed (grounded) metal plate 5 which, in this example, is 1.5 cm below the outlet 3a.

As will be described below, experiments were carried out using formulations consisting of different concentrations of different polymers dissolved in a solvent both with and without the incorporation of a suspension of inert particulate material. The voltage applied by the high voltage source 4 was kept within a constant range in order to isolate the effects of flow rate on the electrostatic processing. The droplet spread or swath angle α and the maximum flow rate for stable droplet formulation were examined for the various different formulations as will be described below. The swath angle α (that is the angle α subtended at the nozzle 3a by the deposition pattern produced on the metal plate 5 (assuming that deposition pattern is roughly circular)) was determined at a formulation flow rate of 7.2 ml per hour (2 microliters per second) by examining the droplets spread on the earthed plate 5 microscope. Photographs of the spraying characteristics were taken using a digital camera.

FIG. 2 shows a graph for illustrating the effects of addition of polymer and suspended inert particulate material to a solvent or liquid mixture which, on its own, will not form a stable cone and jet to enable EHD processing because it is too highly electrically conductive.

FIG. 2 shows a graph of increasing stability rating against increased polymer concentration with line X showing the change in sprayability with increasing polymer concentration of a formulation that does not contain suspended particulate material and line Y showing the change in sprayability with increasing polymer concentration of a formulation containing suspended particulate material. The stability of the spray produced by EHD processing was assessed visually and determined by two parameters, the swath angle α and the maximum flow rate for which droplet production occurs.

Line X in FIG. 2 shows that the EHD spraying characteristics of the polymer formulation without suspended particulate material has three characteristic zones, zones A, B and C. In zone A, when the polymer concentration is still very low, spitting is observed from an unstable cone jet. However, as the polymer concentration is increased, the spraying becomes increasingly more stable. FIG. 3a shows a photograph illustrating spraying characteristics in zone A.

In zone B, stable spraying is observed with relatively little change in stability with increasing polymer concentration. FIG. 3b shows a photograph illustrating the spraying characteristics in zone B.

In zone C, the further increasing concentration of polymer causes an increase in viscosity inhibiting breaking up of the jet into droplets and resulting in a continuous stream of liquid. FIG. 3c shows a photograph illustrating spraying conditions in zone C.

It can thus be seen from line X, in FIG. 2 and the photographs shown in FIGS. 3a to 3c that the addition of polymer to a normally unsprayable liquid can make that liquid sprayable but that the stability of the EHD processing or spraying is very much dependent upon the polymer concentration.

Line Y in FIG. 2 shows the effect of suspending inert particulate material within the formulation and FIGS. 4a, b and c show the spraying characteristics observed for polymer concentration regions corresponding to zones A, B and C in FIG. 2. As can be seen from FIG. 2 and the photographs shown in FIGS. 4a, b and c, the incorporation of the suspended particulate material into the formulation does not significantly affect the stability of the EHD spraying in the region of zone B. However, the incorporation of the suspended particulate material markedly increases the stability in zones A and C, making the stability to EHD spraying of the formulation much less sensitive to the concentration of polymer within the formulation enabling, for example, a lower concentration of polymer to be used if desired. In addition, generally, the swath angle α increased when particulate material was suspended in the formelation, especially in those formulations having a lower polymer concentration. In each example, either an equivalent or increased flow rate was achieved by the addition of the suspended particulate material. In addition, increasing the amount of particulate material suspended within the formulation showed a similar or larger increase in both swath angle α and maximum obtainable flow rate for stable spraying.

Various experiments from which the graph shown in FIG. 2 was derived will now be described in detail.

EXAMPLE 1

In this example, the formulation consisted of polyvinylpyrrolidone of molecular weight 40000 (PVP 40 k) dissolved in ethanol (EtOH) with and without the addition of inert particulate material in the form of sugar. Experiments were carried out for polymer concentrations ranging from 40 mg (milligrams) of PVP 40 k per ml (milliliter) of ethanol (that is 4.0 mg of PVP 40 k added to each ml of ethanol) to over 520 mg of PVP 40 k per ml of ethanol: 1) without any inert particulate material; 2) with a low concentration of sugar (0.1 grams per ml of ethanol); and 3) with a relatively high concentration of sugar (0.5 grams per ml of ethanol).

FIG. 5a shows a bar chart of droplet spread (i.e. the diameter or average width of the droplet deposition pattern on the earthed plate) measured in cm as described above against polymer concentration for these three cases which FIG. 5b shows a bar chart of maximum flow rate in ml/hr against polymer concentration for these cases with a voltage drop of 4.7 kV per cm, that is with the voltage applied by the high voltage source being about 7 kV as in the example described above. The white bars show the results obtained for the formulation without particulate material, the vertical stripe bars show the results obtained for the formulation with the relatively low concentration of inert particulate material and the horizontal stripe bars show the results obtained for the formulation having the relatively high concentration of inert particulate material.

As can be seen from FIGS. 5a and 5b, the higher the concentration of PVP 40 k in the formulation, the more sprayable the formulation becomes. Morever, suspending inert particulate material within the formulation improves the sprayability of those formulations with a polymer concentration from 40 mg per ml of ethanol to 180 mg per ml of ethanol. (The arrows in FIG. 5b indicate that the maximum flow rate for a particulate formulation has not been reached within the tested range, that is at 16 ml per hour the resultant spray was still so stable that stability could be expected to be maintained for even higher flow rates.)

The maximum obtainable flow rate can be seen from FIG. 5b to increase with increasing concentration of inert particulate material with the largest increase in maximum obtainable flow rate occurring for polymer concentrations in the range 40 mg per ml of ethanol to 180 mg per ml of ethanol, which corresponds to zone A shown in FIG. 2.

For polymer concentrations in the range 180 mg per ml of ethanol to 320 mg per ml of ethanol (corresponding to zone B in FIG. 2), the addition of polymer alone is sufficient to stabilise spraying and the effect of addition of the suspended particulate material is less clearly defined. For polymer concentrations from 320 mg per ml of ethanol to 560 mg per ml of ethanol (corresponding to zone C in FIG. 2), the formulation without the suspended particulate material becomes progressively less sprayable as the increasing viscosity collapses the jet into a stream (as can be seen from FIG. 3c). For these high viscosity formulations, the addition of the solid particulate material restores the spread of the jet making atomisation by electrohydrodynamic processing possible as can be seen by comparing FIGS. 3c and 4c. Within this higher viscosity range, the maximum obtainable flow rate was not significantly affected by the addition of the particulate material. At very high concentrations of polymer (520 mg per ml of ethanol and 560 mg per ml of ethanol), the jet tended to collapse into a stream, regardless of the addition of solid particulate material.

EXAMPLE 2

In this example, the formulation consisted of PVP 360 k (that is PVP of 360,000 molecular weight) dissolved in ethanol with and without the incorporation of suspended particulate material in the form of sugar, again at both high and low concentrations. FIGS. 6a and 6b show bar charts similar to FIGS. 5a and 5b respectively, to illustrate the change in droplet spread and maximum flow rate for concentrations of PVP 360 k ranging from 1 mg per ml of ethanol to 45 mg per ml of ethanol with the white bars again showing the results obtained without suspended particulate material in the formulation, the vertical stripe bars showing the results obtained from a formulation incorporating a low concentration of sugar, (again 0.1 grams per ml of ethanol) and the horizontal stripe bars showing the results for a relatively high concentration of sugar (again 0.5 grams per ml of ethanol). Again, the droplet spread shown in FIG. 6a was measured with a flow rate of 7.2 ml per hour and the maximum obtainable flow rate shown in FIG. 6a was measured at a field strength of 4.7 kV per cm.

EXAMPLE 3

Example 3 differs from example 2 in that the sugar was replaced by starch as the particulate material. Again, experiments were carried out with both a low concentration (0.1 grams per ml of ethanol) and a high concentration (0.5 grams per ml of ethanol) of starch particulates suspended in the formulation. Again, the white bar show results obtained without particulate material, the vertical stripe bars show results obtained with a low concentration of particulate material suspended in the formulation and the horizontal stripe bars show the results obtained with a high concentration of particulate material suspended in the formulation.

As can be seen from FIGS. 6a to 7b, the EHD processing characteristics of the formulation improved with the addition of suspended particulate material (either sugar or starch) as the polymer concentration was increased to 2 mg per ml of ethanol (corresponding to zone A in FIG. 2). With polymer concentrations of 4 mg per ml of ethanol and 6 mg per ml of ethanol (corresponding to zone B in FIG. 2) stable spraying was achieved. Above 6 mg per ml of ethanol (corresponding to zone C in FIG. 2), the spray rapidly collapsed in those formulations which did not contain suspended particulate material. The largest increases in maximum obtainable flow rate as a result of incorporation of suspended particulate material occurred at higher polymer concentrations (10 mg per ml of ethanol to 45 mg per ml of ethanol). As can be seen from FIGS. 6*a* and 7*a*, the incorporation of particulate material in suspension significantly increased the droplets spread or swath angle and the presence of the solid particulates in suspension was beneficial across the whole range of polymer concentrations. An upper limit was reached at 45 mg of polymer per ml of ethanol because, with such a high concentration of polymer, the EHD processing resulted in fibre production rather than droplet production, regardless of whether or not solid particulate material suspended in the formulation.

EXAMPLE 4

In this example, the polymer used was a low viscosity ethylcellulose formulation consisting of 5% by volume ethylcellulose in a 80:20 by volume toluene:ethanol mixture and having a viscosity of 15 centipoise (cp) at 25 degrees Celsius. This ethylcellulose formulation is referred to herein as $_{lo}$ethylcellulose ($_{lo}$EC). Four different polymer formulations were provided with the ethylcellulose formulation in two different concentrations in ethanol (20 mg per ml of ethanol and 100 mg per ml of ethanol) and in two different concentrations (20 mg per ml of solvent and 100 mg per ml of solvent) in a solvent consisting of a 3:7 by volume mix of ethanol:water ($EtOH:H_2O$). The experiments were carried out with each of these formulations without any particulate material suspended in the formulation and with 0.5 grams of starch particulate material per ml of solvent (ethanol or ethanol:water) suspended in the formulation. Again, FIGS. 8*a* and 8*b* show the droplets spread and maximum flow rates, respectively, with the droplet spread being obtained at a flow rate of 7.2 ml per hour and the maximum obtainable flow rate being observed at a field strength of 4.7 kV per cm. In FIGS. 8*a* and 8*b*, the white bars show the results obtained without starch in suspension while the horizontal stripe bars show the results obtained when the formulation incorporated the starch.

As can be seen from FIG. 8*a*, the incorporation of particulate material in suspension significantly increased the droplet spread for the formulations having the lower concentration (20 mg per ml of solvent) of polymer and also significantly improved the maximum flow rate for those concentrations.

EXAMPLE 5

In this example, the polymer used was again an ethylcellulose formulation, in this case a high viscosity formulation consisting of Ethocel (trade name) Standard 100 Premium Ethylcellulose (supplied by the Dow Chemical Company) having a viscosity of 100 cp at 25 degrees Celsius. This polymer is referred to herein as $_{hi}$ethylcellulose ($_{hi}$EC). The solvent was ethanol. Two different polymer concentration formulations were tested, a first polymer concentration with 8 mg of polymer per ml of ethanol and a second concentration with 40 mg of polymer per ml of ethanol. In addition, these two polymer formulations were tested both with and without the incorporation of starch particulates in suspension. Where the suspension was added, the concentration of particulate was 0.5 grams per ml of ethanol. The white bars in FIGS. 9*a* and 9*b* show the results obtained where the formulation did not contain the starch particulate material in suspension while the horizontal stripe bars show the results obtained when the formulation incorporated the suspended particulate material.

As can be seen from FIG. 9*b*, the maximum obtainable flow rate was increased when solids were added to the lower polymer concentration formulation and continued to be large for the higher polymer concentration formulation, regardless of the addition of solid particulate material.

EXAMPLE 6

Table 1 shows the results of experiments carried out with different glycerol formulations with and without the incorporation of inert particles in the form of 1 μm (micrometer) diameter polytetrafluorethylene beads ("PTFE" in the table) or 30 μm glass beads ("glass" in the table).

TABLE 1

| Formula | Voltage (kV) | Spread (cm) | Sprayability (7.2 ml/hr; or 15 ml/hr) |
|---|---|---|---|
| 100% glycerol | 6.3-8.0 | 0.5 | streaming |
| 100% glycerol- | 6.83-9.0 | 1 | outer = solids; inner = liquid |

TABLE 1-continued

| Formula | Voltage (kV) | Spread (cm) | Sprayability (7.2 ml/hr; or 15 ml/hr) |
|---|---|---|---|
| 10% glass 90% glycerol-10% EtOH | >5.9 | 0.5 | streaming |
| 90% glycerol-10% EtOH-10% PTFE | 7.0-8.0 | 0.8 | outer = solids; inner = liquid |
| 80% glycerol-20% EtOH | >6.3 | 0.5 | streaming |
| 80% glycerol-20% EtOH-10% PTFE | 6.0-8.0 | 1 | outer = solids; inner = liquid |
| 70% glycerol-30% EtOH | 5.0-8.5 | 0.5 | streaming |
| 70% glycerol-30% EtOH-10% PTFE | 5.3-9.7 | 0.6 | outer = solids; inner = liquid; larger spread (1.1 cm) @ 15 ml/hr |
| 50% glycerol-50% EtOH | 6.0-9.0 | 0.7 | outer = solids; inner = liquid; larger spread (1.2 cm) @ 15 ml/hr |
| 50% glycerol-50% EtOH-10% PTFE | 5.0-8.0 | 1.5 | sprays well; larger spread (1.7 cm) @ 15 ml/hr |

Due the highly viscous nature of the solutions illustrated by Table 1, clearly defined zones A, B and C could not be determined. As illustrated in Table 1 and by the photograph shown in FIG. 10a, streaming occurred for all ratios of glycerol to ethanol tested within the bounds for providing sustainable suspension. However, upon adding approximately 10% by volume loading of inert particles (glass or PTFE beads), an enhancement in the sprayability of the formulations was noted as well as an increase in the swath angle as shown by the photograph shown in FIG. 10b. In these cases, the spray comprised an outer mist of finer droplets with an inner mist of larger less mobile droplets so that the deposition pattern on the earth plate consisted of outer discrete droplets (outer=solids in Table 1) with an inner coalesced liquid region (inner=liquid in Table 1) resulting from, for example, agglomeration of some particulates reducing their lateral mobility and/or the high viscosity of the liquid impeding the free movement of individual particles. In support of the second theory, a larger increase in swath angle was achieved with a larger percentage of ethanol in the formulation.

EXAMPLE 7

Table 2 shows the effect of adding inert particulate material in suspension to a polymer formulation consisting of $_{hi}$ethylcellulose ($_{hi}$EC) at a concentration of 60 mg per ml of ethanol and 80 mg per ml of ethanol. In this case, the inert particulate material suspended in the formulation comprise 30 μm (micrometer) inert glass beads suspended at a concentration of 0.1 grams per ml of ethanol.

TABLE 2

| Formula | Voltage (kV) | Spread (cm) | Sprayability (7.2 ml/hr; or 15 ml/hr) |
|---|---|---|---|
| $_{hi}$EC(60 mg) + EtOH (1 ml) | 5.95 | 1.2 | good spray |
| $_{hi}$EC(60 mg) + EtOH (1 ml) + glass (0.1 g) | 4.79-5 | 1.5 | spreads out more |
| $_{hi}$EC(80 mg) + EtOH (1 ml) | 7.56 | 0.8 | one moving jet |
| $_{hi}$EC(80 mg) + EtOH (1 ml) plus glass (0.1 g) | 7.5 | 1.5 | good spray |

As can be seen from Table 2, incorporating the inert particulate material into the polymer formulation increased the swath angle for the lower polymer concentration formulation and for the higher polymer concentration increased the stability of the spraying.

FIGS. 11a and 11b show the spray characteristics for the 80 mg per ml formulation without and with suspended particulate material. As can be seen from Table 2 and FIGS. 11a and 11b incorporation of the particulate material improves the EHD spraying characteristics.

It will, of course, be appreciated that the formulations described above where the inert particulate material comprises glass beads will generally not be used for inhalation or topical application to a body surface. However, the fact that the effects (increased maximum flow rate and increased swath angle) are observed when using glass particles and polymer beads means that these effects should be observed with almost any biologically compatible inert material that can be suspended within the formulation.

The particulate material maybe maintained in suspension in any suitable manner known to those skilled in the art. For example, the reservoir may incorporate a mechanical or other stirrer that maintains the suspension. As another possibility, the formulation may include a viscosity enhancer such as glycerol, gum arabic or a cellulose polymer derivative such as hydroxypropylmethylcellulose (HPMC), hydroxypropylcellulose (HPC) or carboxymethylcellulose (CMC) or hydroxyethylcellulose (HEC). Other ways of maintaining suspensions are described at for example, pages 50 to 59 of the text book entitled "Solid/Liquid Dispersions" edited by Tadros, Th. F. Academic Press 1987. As another possibility, a polymeric surfactant such as one of the ATLOX series of polymeric surfactants described in the Uniqema Technical Bulletin 00-4 may be used to maintain the suspension.

As will be seen from the above examples, suspension of inert particulate material in a polymer formulation, facilitates electrohydrodynamic processing of the formulation, enabling stable spraying at higher f low rates and providing an increased swath angle so that, for a given distance of the outlet 3a from the deposition surface, the resultant spray covers a larger area of the target surface.

FIG. 12 shows a very diagrammatic cut away view of one example of a dispenser 200 that may be used to effect electrohydrodynamic processing of the formulations described above. As can be seen in FIG. 12 the dispenser comprises a housing 20 having a first chamber 21 containing a voltage source 22 such as a battery coupled via a switch SW to a high voltage generator 23 and to a pump 24 which is coupled to a liquid formulation reservoir 25 to pump formulation from the reservoir to a tube (shown part cut-away) having an outlet 30a. The tube 30 extends from the first chamber 21 into a second chamber 26 including a dispensing outlet 20a of the housing. In this example, the tube 30 is electrically insulating and carries an electrode 31 which is coupled to a high voltage output line 23a of the high voltage generator. A conductive core or rod 32 supported within the liquid outlet tube 30 is coupled to the earth or negative terminal of the voltage source 22 via line 22a.

In operation of this dispensing device when the switch SW is activated, an electric field is generated between the first and second electrodes 31 and 32 and liquid formulation is pumped from the reservoir 25 to the liquid outlet 30a by the pump 24. Liquid issuing from the outlet 30a is thus subject to a high electric field as described above resulting in electrohydrodynamic comminution of the liquid to produce a cloud or mist of droplets which exit the device via the dispensing outlet 20a.

Incorporation of suspended particulate material within the formulation as described above enables higher flow rates so that a larger dose of medicament can be delivered within a given time and also enables, as described above, an increased swath angle thereby facilitating closer range spraying.

The dispensing device may be designed as a nasal inhaler, in which case the formulation will also contain an active ingredient to be delivered via the nasal passages. The active ingredient may be a medicament for use in the treatment by way of therapy, surgery or diagnosis of an animal body such as a human being or otherwise to improve quality of life. The medicament may be an antibiotic, anti-cancer agent, or other pharmaceutical product, a vaccine, a protein, an enzyme, DNA or DNA fragments or other biological products, an anti-inflammatory, a vitamin, an antiseptic, morphine or other pain killing drug, nicotine and so on. Further, examples of dispensing devices in the form of nasal inhalers that may be used to dispense the above formulations are described in WO 00/35524.

As another example, the dispensing device may be designed to enable topical application of an active ingredient to a body surface, such as an area of skin, or a wound surface. In this case, the increased swath angle enables topical application over a wider area.

WO 98/03267 describes examples of other dispensing devices that may be used to dispense a formulation in accordance with the present invention.

The dispensing device, may as another possibility, be designed to deliver a cloud or spray in which the active ingredient is a pesticide or other garden product with, again, the increased swath angle provided by the incorporation of the suspended particulate material enabling the device to be positioned closer to the area to be sprayed (for example, a leaf surface) while still maintaining the desired coverage area, so facilitating and ensuring that the active ingredient carried by the cloud or droplet spray is deposited onto the desired target surface.

Further examples of electrohydrodynamic comminution devices that may be used to dispense a formulation in accordance with the present invention are described in, for example, WO 94/12285, WO 94/14543, WO 95/26235, WO 00/35524, WO 99/07478 and WO 00/03267, the whole contents of each of which are hereby incorporated by reference.

The particulate material may be formed of any one or more of a number of different types of materials with the only constraint being that the particulate material is biologically compatible and is substantially insoluble in and can be suspended in the polymer formulation. Examples of types of particulate material are: chalk or kaolin particles or particles of another biologically compatible polymer that is insoluble in the polymer formulation; where the dosage form is for oral delivery, flavourings such as sweeteners both artificial and natural (such as simple and complex sugars) and/or effervescent particles, that is particles that effervesce in the mouth but not in the polymer formulation; particles of active ingredient. All of these types of particles may be solid, hollow or porous. Other types of particles that may be used include: micro capsules (formed of, for example, another biologically compatible polymer that is insoluble in the polymer formulation); that are inert (i.e. contain air, gas or an inert liquid) or contain an active ingredient or ingredients in solid, granular, liquid or gel form; polymer particles having dissolved or dispersed therein an active ingredient; particles of active ingredient coated with a coating material that is insoluble in the polymer formulation such as another biologically compatible polymer. Any one or more of these types of particles may be used and, where the particles are or incorporate an active ingredient one or more different active ingredients may be used, depending upon the properties required of the dosage form. The particles may be of the same size (mono-dispersed) or may have a range of sizes, may be smaller than 1 mm in diameter (assuming a generally spherical shape) and typically may have a diameter or diameters in the range from sub micron to 100 microns. The particles need not necessarily be spherical but could be ellipsoidal, granular, shard-like or rod-like, for example.

As another possibility, at least a proportion of the suspended particulate material may comprise active ingredient. The incorporation of the active ingredient into the formulation as a particulate suspension facilitates delivery by electrohydrodynamic processing of active ingredients in the form of salts which, due to their polar nature, could not generally be delivered by electrohydrodynamic processing if dissolved within the formulation because the resulting solution would be too highly conductive.

In the above described examples, the solvent used is ethanol or an ethanol-water mixture, other solvents may be used. Also, other biologically compatible polymers may be used. In addition, the polymer formulation need not necessarily be a solution but could be a polymer melt in which case, of course, the particulate material should remain solid and not itself melt within the molten polymer. The particulate material may be designed to degrade, dissolve or disintegrate during use, for example after inhalation or topical application. As an example, the particulate material may comprise a biodegradable or dissolvable polymer, which remains solid in the polymer formulation but, after EHD processing, for example after inhalation or topical application, degrades or dissolves. Making the particulate material hollow as discussed above may facilitate this.

Suspending an active ingredient within the formulation not only enables active ingredients that could not otherwise be sprayed (because their aqueous solutions are too electrically conductive) but also enables the possibility of ensuring that the active ingredient is not present in droplets below a certain size (determined by the particulate size). This may be particularly advantageous where the formulation is to be dispensed from an inhaler because it should ensure that non fraction of the active ingredient will be carried to the respiratory system in satellite droplet form.

Formulations in accordance with the present invention may also enable effective localisation of the particulate matter evenly over a target surface by virtue of the "sticky" action of the polymer which may facilitate delivery of active ingredient where the suspended particulate material includes active ingredient.

In a formulation embodying the invention, the addition of a polymer increases the formulation viscosity, thereby increasing the shelf life of the suspension. As described above, increased flow rate is achieved firstly by adding the polymer and secondly by adding the particulate material in suspension. As seen from the above, the addition of polymer and particulate material in suspension enables some liquids that would otherwise not be sprayable by electrohydrodynamic processing to be made sprayable and moreover increases the swath or deposition angle of the droplets thereby facilitating closer range spraying of viscous liquid. The particulate material may be suspended in the formulation in any conventional manner and need not be micronised because the buffering effect of the polymer during spraying ensures that the cone jet is not disrupted by even relatively large suspended particles. In addition, the spraying characteristics are not significantly adversely affected even with poorly distributed and poorly separated solids in the suspension.

The invention claimed is:

1. A method of providing a droplet spray using an EHD device, for administration to a patient by inhalation, which method comprises:
supplying a liquid formulation to an outlet of said EHD device and subjecting liquid issuing from the outlet to an electric field that causes the liquid to break up into droplets via aerosolization of said liquid formulation using said EHD device,
wherein said liquid formulation comprises a solution comprising a polymer and a substantially inert biologically-compatible particulate material in a solvent;
wherein the solution comprises 40 mg to 500 mg of polyvinylpyrrolidone of molecular weight 40,000 as the polymer per milliliter of ethanol as the solvent, with 0.1 or 0.5 grams of particulate material per milliliter of ethanol suspended in the solution.

2. A method according to claim 1, wherein the substantially inert, biologically-compatible particulate material comprises a material selected from sugar, starch, and insoluble polymer particles, and mixtures thereof.

3. A method according to, claim 1, wherein the substantially inert, biologically-compatible particulate material also includes at least one active ingredient or particles of at least one active ingredient.

4. A method of providing a droplet spray using an EHD device, for administration to a patient by inhalation, which method comprises:
supplying a liquid formulation to an outlet of said EHD device and subjecting liquid issuing from the outlet to an electric field that causes the liquid to break up into droplets via aerosolization of said liquid formulation using said EHD device,
wherein said liquid formulation comprises a solution comprising a polymer and a substantially inert biologically-compatible particulate material in a solvent;
wherein the solution comprises 40 to 180 mg of polyvinylpyrrolidone of molecular weight 40,000 as the polymer per milliliter of ethanol as the solvent, with 0.1 or 0.5 grams of particulate material per milliliter of ethanol suspended in the solution.

5. A method of providing a droplet spray using an EHD device, for administration to a patient by inhalation, which method comprises:
supplying a liquid formulation to an outlet of said EHD device and subjecting liquid issuing from the outlet to an electric field that causes the liquid to break up into droplets via aerosolization of said liquid formulation using said EHD device,
wherein said liquid formulation comprises a solution comprising a polymer and a substantially inert biologically-compatible particulate material in a solvent;
wherein the solution comprises 2 to 45 mg of polyvinylpyrrolidone of molecular weight 360,000 as the polymer per milliliter of ethanol as the solvent, with 0.1 or 0.5 grams of particulate material per milliliter of ethanol suspended in the solution.

* * * * *